(12) United States Patent
Freundlich et al.

(10) Patent No.: US 6,618,620 B1
(45) Date of Patent: Sep. 9, 2003

(54) APPARATUS FOR CONTROLLING THERMAL DOSING IN AN THERMAL TREATMENT SYSTEM

(75) Inventors: David Freundlich, Haifa (IL); Jacob Vortman, Haifa (IL); Roni Yagel, Modiin (IL); Shuki Vitek, Haifa (IL); Naama Brenner, Haifa (IL)

(73) Assignee: TxSonics Ltd., Tirat Carmel (IL)

( * ) Notice: Subject to any disclaimer, the term of this patent is extended or adjusted under 35 U.S.C. 154(b) by 0 days.

(21) Appl. No.: 09/724,670

(22) Filed: Nov. 28, 2000

(51) Int. Cl.$^7$ .............................................. A61N 1/368
(52) U.S. Cl. ............................ 607/27; 607/89; 607/96; 607/115; 606/27; 600/437; 604/22; 601/3
(58) Field of Search ................................ 607/27, 2, 88, 607/89, 96, 98, 99, 100, 101, 113, 115; 606/27; 600/437, 439, 459; 128/898; 604/19, 20, 21, 22; 601/2, 3

(56) References Cited

U.S. PATENT DOCUMENTS

| | | | |
|---|---|---|---|
| 4,441,486 A | * | 4/1984 | Pounds ........................... 601/3 |
| 4,549,533 A | | 10/1985 | Cain et al. |
| 4,586,512 A | * | 5/1986 | Do-huu et al. .............. 600/459 |
| 4,858,597 A | | 8/1989 | Kurtze et al. |

(List continued on next page.)

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986.

Todd Fjield, et al., "The Combined Concentric–Ring and Sector–Vortex Phased Array for MRI Guided Ultrasound Surgery", IEEE Transactions on Ultrasonics, Ferroelectrics and Frequency Control, vol. 44, No. 5, pp. 1157–1167, Sep. 1997.

Nathan McDannold, et al., "MRI Evaluation of Thermal Ablation of Tumors and Focused Ultrasound", JMRI vol. 8, No. 1, pp. 91–100, Jan./Feb. 1998.

Kullervo Hynyen et al., "Principles of MR–Guided Focused Ultrasound", Chapter 25, pp. 237–243.

Harvey E. Cline, Ph.D., et al., "Focused US System for MR Imaging–Guide Tumor Ablation", Radiology vol. 194, No. 3, pp. 731–738, Mar. 1995.

*Primary Examiner*—Teresa Walberg
*Assistant Examiner*—Fadi H. Dahbour
(74) *Attorney, Agent, or Firm*—Bingham McCutchen LLP

(57) ABSTRACT

A thermal treatment system including a heat applying element for generating thermal doses for ablating a target mass in a patient, a controller for controlling thermal dose properties of the heat applying element, an imager for providing preliminary images of the target mass and thermal images during the treatment, and a planner for automatically constructing a treatment plan, comprising a series of treatment sites that are each represented by a set of thermal dose properties. The planner automatically constructs the treatment plan based on input information including one or more of a volume of the target mass, a distance from a skin surface of the patient to the target mass, a set of default thermal dose prediction properties, a set of user specified thermal dose prediction properties, physical properties of the heat applying elements, and images provided by the imager. The default thermal dose prediction properties are preferably based on a type of clinical application and include at least one of thermal dose threshold, thermal dose prediction algorithm, maximum allowed energy for each thermal dose, thermal dose duration for each treatment site, cooling time between thermal doses, and electrical properties for the heat applying element. The user specified thermal dose prediction properties preferably include at least one or more of overrides for any default thermal dose prediction properties, treatment site grid density; and thermal dose prediction properties not specified as default thermal dose prediction properties from the group comprised of thermal dose threshold, thermal dose prediction algorithm, maximum allowed energy for each thermal dose, thermal dose duration for each treatment site cooling time between thermal doses, and electrical properties for the heat applying element.

22 Claims, 11 Drawing Sheets

U.S. PATENT DOCUMENTS

| | | | |
|---|---|---|---|
| 4,865,042 A | | 9/1989 | Umemura et al. |
| 4,888,746 A | | 12/1989 | Wurster et al. |
| 5,247,935 A | | 9/1993 | Cline et al. |
| 5,275,165 A | | 1/1994 | Ettinger et al. |
| 5,291,890 A | | 3/1994 | Cline et al. |
| 5,307,812 A | | 5/1994 | Hardy et al. |
| 5,323,779 A | | 6/1994 | Hardy et al. |
| 5,327,884 A | | 7/1994 | Hardy et al. |
| 5,368,031 A | | 11/1994 | Cline et al. |
| 5,368,032 A | | 11/1994 | Cline et al. |
| 5,435,304 A | * | 7/1995 | Oppelt et al. ............... 600/439 |
| 5,443,068 A | | 8/1995 | Cline et al. |
| 5,485,839 A | | 1/1996 | Aida et al. |
| 5,490,840 A | | 2/1996 | Uzgiris et al. |
| 5,501,655 A | * | 3/1996 | Rolt et al. ..................... 601/3 |
| 5,507,790 A | | 4/1996 | Weiss |
| 5,520,188 A | | 5/1996 | Hennige et al. |
| 5,526,814 A | | 6/1996 | Cline et al. |
| 5,526,815 A | * | 6/1996 | Granz et al. ................. 600/439 |
| 5,573,497 A | | 11/1996 | Chapelon |
| 5,590,657 A | | 1/1997 | Cain et al. |
| 5,665,054 A | | 9/1997 | Dory |
| 5,694,936 A | * | 12/1997 | Fujimoto et al. ............ 600/439 |
| 5,711,300 A | | 1/1998 | Schneider et al. |
| 5,722,411 A | | 3/1998 | Suzuki et al. |
| 5,743,863 A | | 4/1998 | Chapelon |
| 5,769,790 A | | 6/1998 | Watkins et al. |
| 5,823,962 A | * | 10/1998 | Schaetzle et al. ........... 600/439 |
| 5,873,845 A | | 2/1999 | Cline et al. |
| 6,042,556 A | * | 3/2000 | Beach et al. .................... 601/3 |
| 6,128,522 A | | 10/2000 | Acker et al. |
| 6,267,734 B1 | * | 7/2001 | Ishibashi et al. ................ 601/2 |

* cited by examiner

APPARATUS FOR CONTROLLING THERMAL DOSING IN AN THERMAL TREATMENT SYSTEM

FIELD OF INVENTION

The present invention relates generally to thermal treatment systems, and more particularly to a method and apparatus for controlling thermal dosing in a thermal treatment system.

BACKGROUND

Thermal energy, such as generated by high intensity focused ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers driven by electric signals to produce ultrasonic energy have been suggested that may be placed external to the patient but in close proximity to the tissue to be ablated. The transducer is geometrically shaped and positioned such that the ultrasonic energy is focused at a "focal zone" corresponding to a target tissue region within the patient, heating the target tissue region until the tissue is coagulated. The transducer may be sequentially focused and activated at a number of focal zones in close proximity to one another. This series of "sonications" is used to cause coagulation necrosis of an entire tissue structure, such as a tumor, of a desired size and shape.

In such focused ultrasound systems, the transducer is preferably geometrically shaped and positioned so that the ultrasonic energy is focused at a "focal zone" corresponding to the target tissue region, heating the region until the tissue is necrosed. The transducer may be sequentially focused and activated at a number of focal zones in close proximity to one another. For example, this series of "sonications" may be used to cause coagulation necrosis of an entire tissue structure, such as a tumor, of a desired size and shape.

By way of illustration, FIG. 1A depicts a phased array transducer 10 having a "spherical cap" shape. The transducer 10 includes a plurality of concentric rings 12 disposed on a curved surface having a radius of curvature defining a portion of a sphere. The concentric rings 12 generally have equal surface areas and may also be divided circumferentially 14 into a plurality of curved transducer sectors, or elements 16, creating a "tiling" of the face of the transducer 10. The transducer elements 16 are constructed of a piezoelectric material such that, upon being driven with a sinus wave near the resonant frequency of the piezoelectric material, the elements 16 vibrate according to the phase and amplitude of the exciting sinus wave, thereby creating the desired ultrasonic wave energy.

As illustrated in FIG. 1B, the phase shift and amplitude of the respective sinus "drive signal" for each transducer element 16 is individually controlled so as to sum the emitted ultrasonic wave energy 18 at a focal zone 20 having a desired mode of focused planar and volumetric pattern. This is accomplished by coordinating the signal phase of the respective transducer elements 16 in such a manner that they constructively interfere at specific locations, and destructively cancel at other locations. For example, if each of the elements 16 are driven with drive signals that are in phase with one another, (known as "mode 0"), the emitted ultrasonic wave energy 18 are focused at a relatively narrow focal zone. Alternatively, the elements 16 may be driven with respective drive signals that are in a predetermined shifted-phase relationship with one another (referred to in U.S. Pat. No. 4,865,042 to Umemura et al. as "mode n"). This results in a focal zone that includes a plurality of 2n zones disposed about an annulus, i.e., generally defining an annular shape, creating a wider focus that causes necrosis of a larger tissue region within a focal plane intersecting the focal zone. Multiple shapes of the focal spot can be created by controlling the relative phases and amplitudes of the emmitted energy from the array, including steering and scanning of the beam, enabling electronic control of the focused beam to cover and treat multiple of spots in the defined zone of a defined tumor inside the body.

More advanced techniques for obtaining specific focal distances and shapes are disclosed in U.S. patent application Ser. No. 09/626,176, filed Jul. 27, 2000, entitled "Systems and Methods for Controlling Distribution of Acoustic Energy Around a Focal Point Using a Focused Ultrasound System;" U.S. patent application Ser. No. 09/556,095, filed Apr. 21, 2000, entitled "Systems and Methods for Reducing Secondary Hot Spots in a Phased Array Focused Ultrasound System;" and U.S. patent application Ser. No. 09/557,078, filed Apr. 21, 2000, entitled "Systems and Methods for Creating Longer Necrosed Volumes Using a Phased Array Focused Ultrasound System." The foregoing (commonly assigned) patent applications, along with U.S. Pat. No. 4,865,042, are all hereby incorporated by reference for all they teach and disclose.

It is significant to implementing these focal positioning and shaping techniques to provide a transducer control system that allows the phase of each transducer element to be independently controlled. To provide for precise positioning and dynamic movement and reshaping of the focal zone, it is desirable to be able to alter the phase and/or amplitude of the individual elements relatively fast, e.g., in the $\mu$ second range, to allow switching between focal points or modes of operation. As taught in the above-incorporated U.S. patent application Ser. No. 09/556,095, it is also desirable to be able to rapidly change the drive signal frequency of one or more elements.

Further, in a MRI-guided focused ultrasound system, it is desirable to be able to drive the ultrasound transducer array without creating electrical harmonics, noise, or fields that interfere with the ultra-sensitive receiver signals that create the images. A system for individually controlling and dynamically changing the phase and amplitude of each transducer element drive signal in phased array focused ultrasound transducer in a manner which does not interfere with the imaging system is taught in commonly assigned U.S. patent application Ser. No. [not-yet-assigned; Lyon & Lyon Attorney Docket No. 254/189, entitled "Systems and Methods for Controlling a Phased Array Focussed Ultrasound System,"], which was filed on the same date herewith and which is hereby incorporated by reference for all it teaches and discloses.

Notably, after the delivery of a thermal dose, e.g., ultrasound sonication, a cooling period is required to avoid harmful and painful heat build up in healthy tissue adjacent a target tissue structure. This cooling period may be significantly longer than the thermal dosing period. Since a large number of sonications may be required in order to fully ablate the target tissue site, the overall time required can be significant. If the procedure is MRI-guided, this means that the patient must remain motionless in a MRI machine for a significant period of time, which can be very stressful. At the same time, it may be critical that the entire target tissue structure be ablated (such as, e.g., in the case of a malignant cancer tumor), and that the procedure not take any short cuts just in the name of patient comfort.

Accordingly, it would be desirable to provide systems and methods for treating a tissue region using thermal energy, such as focused ultrasound energy, wherein the thermal dosing is applied in a more efficient and effective manner.

SUMMARY OF THE INVENTION

In accordance with a first aspect of the invention, a thermal treatment system is provided, the system including a heat applying element for generating a thermal dose used to ablate a target mass in a patient, a controller for controlling thermal dose properties of the heat applying element, an imager for providing preliminary images of the target mass and thermal images during the treatment, and a planner for automatically constructing a treatment plan, comprising a series of treatment sites that are each represented by a set of thermal dose properties. By way of non-limiting example only, the heat applying element may apply any of ultrasound energy, laser light energy, radio frequency (RF) energy, microwave energy, or electrical energy.

In a preferred embodiment, the planner automatically constructs the treatment plan based on input information including one or more of a volume of the target mass, a distance from a skin surface of the patient to the target mass, a set of default thermal dose prediction properties, a set of user specified thermal dose prediction properties, physical properties of the heat applying elements, and images provided by the imager. The default thermal dose prediction properties are preferably based on a type of clinical application and include at least one of thermal dose threshold, thermal dose prediction algorithm, maximum allowed energy for each thermal dose, thermal dose duration for each treatment site, cooling time between thermal doses, and electrical properties for the heat applying element. The user specified thermal dose prediction properties preferably include at least one or more of overrides for any default thermal dose prediction properties, treatment site grid density; and thermal dose prediction properties not specified as default thermal dose prediction properties from the group comprised of thermal dose threshold, thermal dose prediction algorithm, maximum allowed energy for each thermal dose, thermal dose duration for each treatment site cooling time between thermal doses, and electrical properties for the heat applying element.

Preferably, the treatment plan ensures that the entire target mass is covered by a series of thermal doses so as to obtain a composite thermal dose sufficient to ablate the entire target mass, and the thermal dose properties are automatically optimized using physiological properties as the optimization criterion. Preferably, the planner limits the thermal dose at each treatment site in order to prevent evaporation or carbonization.

In a preferred embodiment, the planner constructs a predicted thermal dose distribution in three dimensions, illustrating the predicted thermal dose threshold contours of each treatment site in the treatment plan. A User Interface (UI) may also be provided for entering user specified thermal dose prediction properties and for editing the treatment plan once the treatment plan is constructed. A feedback imager for providing thermal images may also be provided, wherein the thermal images illustrate the actual thermal dose distribution resulting at each treatment site. In one embodiment, the imager acts as the feedback imager.

In accordance with another aspect of the invention, a focused ultrasound system is provided, including a transducer for generating ultrasound energy that results in thermal doses used to ablate a target mass in a patient, a controller for controlling thermal dose properties of the transducer, an imager for providing preliminary images of the target, and for providing thermal images illustrating an actual thermal dose distribution in the patient, and a planner for automatically constructing a treatment plan using the preliminary images, the treatment plan comprising a series of treatment sites represented by a set of thermal dose properties used by the controller to control the transducer.

The planner preferably constructs a predicted thermal dose distribution illustrating the predicted thermal dose contours of each treatment site in the treatment plan, wherein after a thermal dose is delivered to a treatment site in the treatment plan, the actual thermal dose distribution is compared to the predicted thermal dose distribution to determine remaining untreated locations within the target mass. The planner preferably automatically evaluates the treatment plan based on the remaining untreated locations and will update the treatment plan to ensure complete ablation of the target mass is achieved by adding treatment sites, removing treatment sites, modifying existing treatment sites, or leaving the treatment plan unchanged. In some embodiments, a user can manually adjust the treatment plan based on the remaining untreated locations.

Preferably, the imager provides outlines of sensitive regions within the patient where ultrasonic waves are not allowed to pass, wherein the processor uses the outlines in constructing the treatment plan so as to avoid exposing the sensitive regions to ultrasound.

In accordance with still another aspect of the invention, a method of controlling thermal dosing in a thermal treatment system is provided, which includes selecting an appropriate clinical application protocol, the selected application protocol having associated with it certain default thermal dosing properties; retrieving relevant magnetic resonant images for thermal dose planning; tracing a target mass on the images; entering user specified thermal dosing properties and selectively modifying the default thermal dosing properties; and automatically constructing a treatment plan representing thermal doses to be applied to treatment sites, the treatment plan based on the default thermal dosing properties and the user specified thermal dosing properties.

In preferred implementations, tracing the target mass can be done manually or automatically, and may include evaluating the target mass to ensure that obstacles including bones, gas, or other sensitive tissue will not interfere with the thermal doses and repositioning a patient or a heat applying element in order to bypass any such obstacles. Preferably, the treatment plan ensures that a target mass receives a composite thermal dose sufficient to ablate the target mass, where automatically constructing the treatment plan includes predicting and displaying a predicted thermal dose distribution. Preferably, automatically constructing the treatment plan further includes calculating limits for each thermal dose to be applied to each treatment site in order to prevent evaporation or carbonation.

In a preferred implementation, the treatment plan may be manually edited, including at least one of adding treatment sites, deleting treatment sites, changing the location of treatment sites, changing thermal dosing properties, and reconstructing the entire treatment plan with new thermal dosing properties.

In one implementation, the method includes applying a low energy thermal dose at a predetermined spot within the target mass in order to verify proper registration, and evaluating said predetermined spot and adjusting and/or re-verifying if necessary. In a following step, the low energy thermal dose could be extended to a full dose sonication that will be evaluated to assess the thermal dosing parameters as a scaling factor for the full treatment.

Other aspects and features of the invention will become apparent hereinafter.

BRIEF DESCRIPTION OF THE DRAWINGS

The drawings illustrate both the design and utility of preferred embodiments of the invention, in which similar elements in different embodiments are referred to by the same reference numbers for purposes of ease in illustration, and wherein:

FIG. 10A illustrates a two dimensional pixel representation of a predicted thermal dose to be applied to a target tissue region.

FIG. 10B illustrates a two dimensional pixel representation of an actual thermal dose resulting from a thermal treatment intended to result in the predicted thermal dose of FIG. 10A.

DETAILED DESCRIPTION OF THE PREFERRED EMBODIMENTS

The invention will now be illustrated by examples that use an ultrasound transducer as the means of delivering energy to a target mass. It will be apparent to those skilled in the art, however, that other energy delivery vehicles can be used. For example, the invention is equally applicable to systems that use laser light energy, radio frequency (RF) energy, microwave energy, or electrical energy converted to heat, as in an ohmic heating coil or contact. Therefore, the following preferred embodiments should not be considered to limit the invention to an ultrasound system.

Figure 1A:
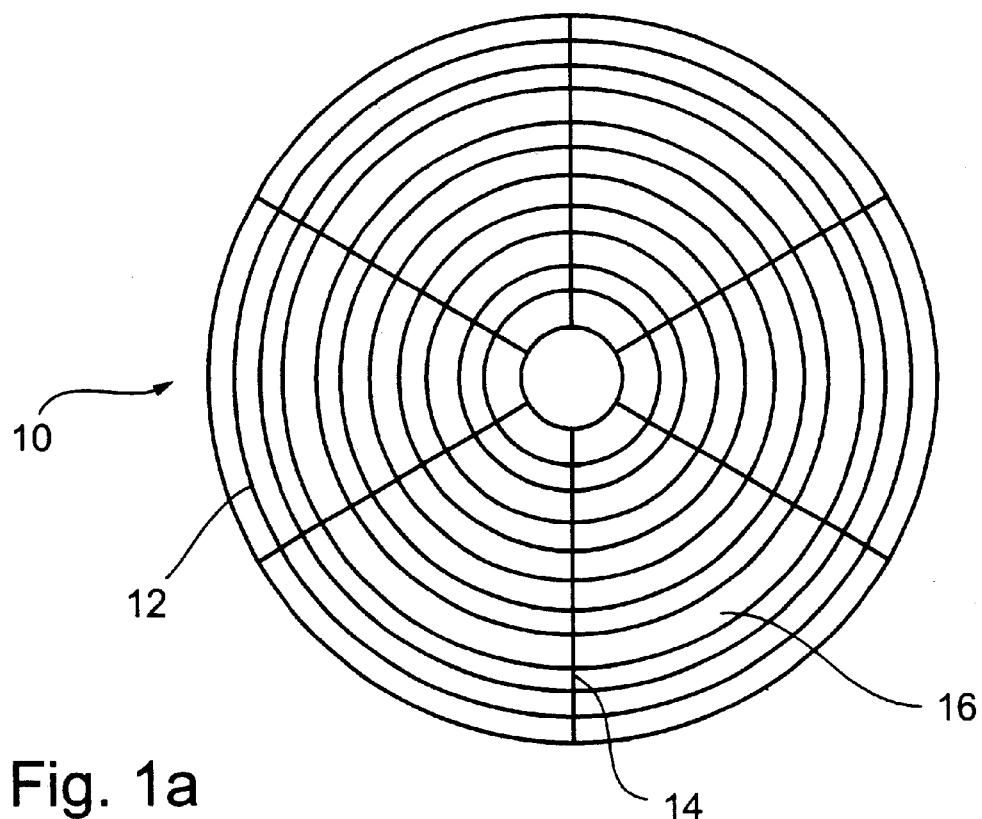
FIG. 1A is a top view of an exemplary spherical cap transducer comprising a plurality of transducer elements to be driven in a phased array as part of a focussed ultrasound system.
Figure 1B:
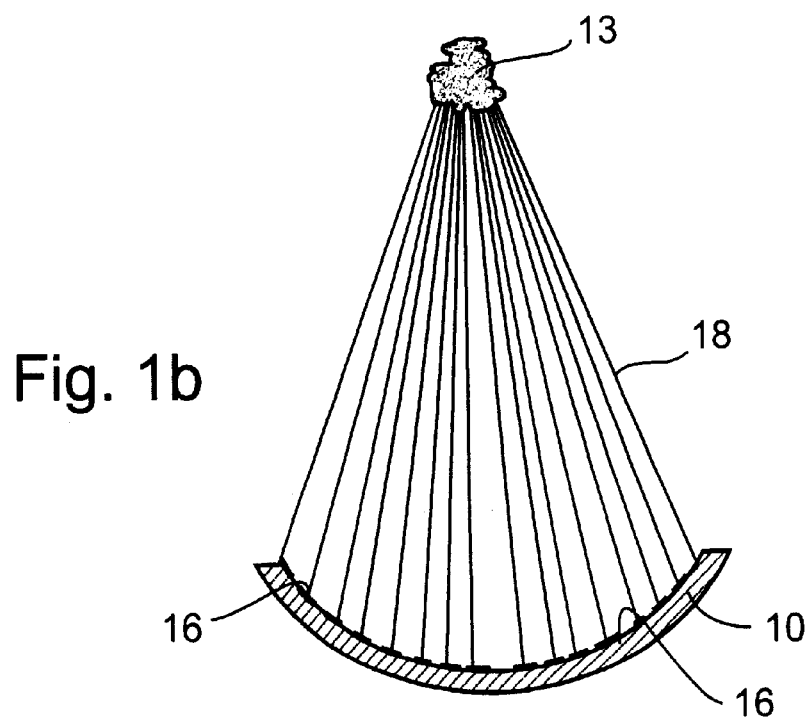
FIG. 1B is a partially cut-away side view of the transducer of FIG. 1A, illustrating the concentrated emission of focused ultrasonic energy in a targeted focal region.
Figure 2:
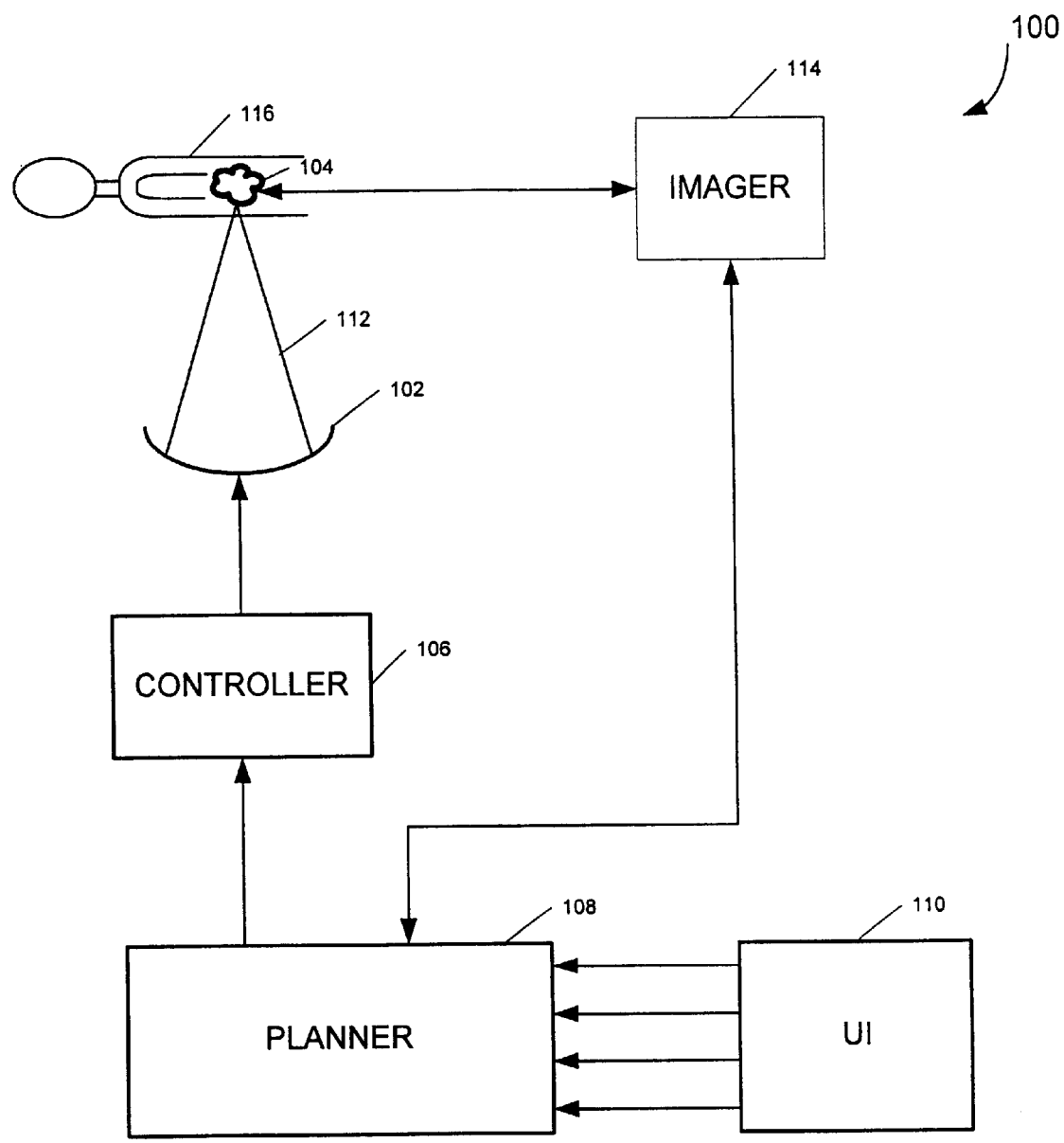
FIG. 2 is simplified schematic block diagram of a thermal treatment system for providing thermal energy dosing of a target tissue region in a patient.

FIG. 2 illustrates a thermal treatment system 100 in accordance with one embodiment of the invention. Thermal treatment system 100 uses a heat applying element 102 to focus an energy beam 112 on a target mass 104, which is typically a tumor within a patient 116. In one preferred implementation, the thermal treatment system 100 is a focused ultrasound system and the heat applying element 102 is a transducer that delivers an ultrasound beam. In this embodiment, the transducer 102 may consist of a spherical cap transducer such as that disclosed in the above-incorporated Umemura patent. It will be appreciated by those skilled in the art that a variety of geometric designs for transducer 102 may be employed. Additionally, alternate embodiments of system 100 will use focused radiators, acoustic lenses, or acoustic reflectors in order to achieve optimal focus of beam 112.

Ultrasound is a vibrational energy that is propagated as a mechanical wave through a target medium. In system 100, transducer 102 generates the mechanical wave by converting an electronic drive signal into mechanical motion. The frequency of the mechanical wave, and therefore ultrasound beam 112, is equal to the frequency of the drive signal. The ultrasound frequency spectrum begins at 20 Khz and typical implementations of system 100 employ frequencies in the range from 0.5 to 10 Mhz. Transducer 102 also converts the electronic drive signal power into acoustic power in ultrasound beam 112. Ultrasound beam 112 raises the temperature of target mass 104 by transferring this power as heat to target mass 104. Ultrasound beam 112 is focused on the target mass 104 in order to raise the temperature of the target mass tissue to a point where the tissue is destroyed. The heat distribution within the tissue is controlled by the intensity distribution in the focal spot of beam 112, the intensity distribution, in turn, is shaped by the interaction of the beam with the tissue and the frequency, duration, and power of beam 112, which are directly related to the frequency, duration, and power of the electronic drive signal.

Figure 3:
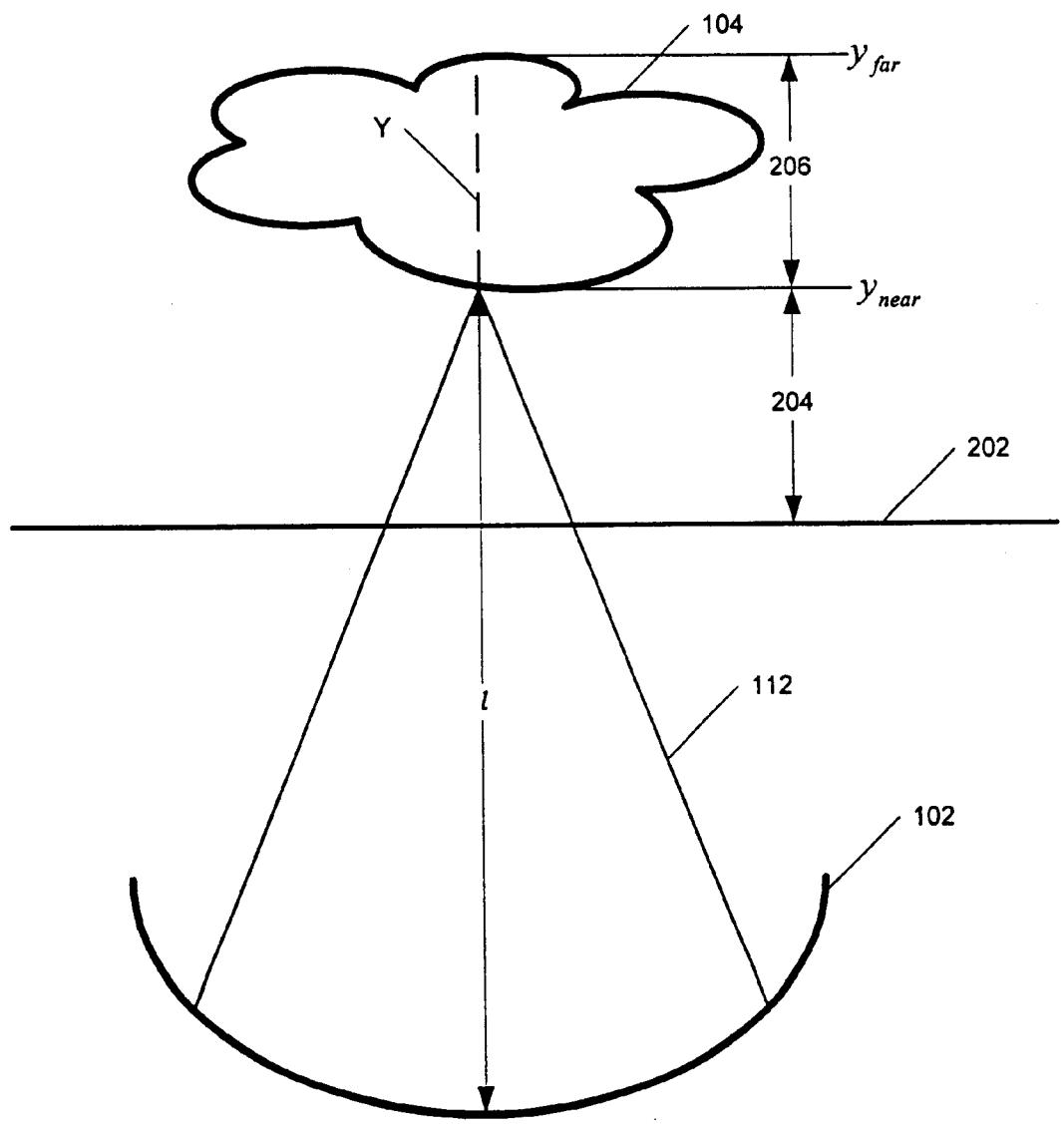
FIG. 3 is a cross-sectional view of an ultrasonic transducer and target tissue mass to be treated in a preferred embodiment of the system of FIG. 2.

As seen in FIG. 3, the transducer 102 focuses beam 112 on a target tissue mass 104, which is within a patient 116 some distance from skin surface 202. The distance from skin surface 202 to target mass 104 is the near field 204, which contains healthy tissue. It is important that tissue in near field 204 is not damaged by beam 112. Energy zone 206 is the target zone for beam 112, wherein energy is transferred as heat to the tissue of the target mass 104. Energy zone 206 is divided into several cross sections of varying depth. Varying the frequency of the electric signal driving transducer 102 can target particular cross sections within energy zone 206.

Two proportionalities illustrate this point: (1) d is proportional to $k_1(v/f)(R/2a)$; and (2) l is proportional to $k_2(v/f)(R/2a)^2$. In (1), d represents the diameter of the focal spot of beam 112. R represents the radius of curvature, and 2a represents the diameter, respectively, of transducer 102. Therefore, the physical parameters associated with transducer 102 are important parameters, as well. In (2), l represents the axial length of the focus of beam 112. Different cross sections can be targeted by changing the frequency f, which will vary the focal length l. In both (1)

and (2), v is the speed of sound in body tissue and is approximately 1540 m/s.

As can be seen, the same parameters that play an important role in determining the focal length l, also play an important role in determining the focal spot diameter d. Because the focal spot will typically be many times smaller than transducer 102, the acoustic intensity will be many times higher in the focal spot as compared to the intensity at the transducer. In some implementations, the focal spot intensity can be hundreds or even thousands of times higher than the transducer intensity. The frequency f also effects the intensity distribution within energy zone 206: The higher the frequency, the tighter the distribution, which is beneficial in terms of not heating near field 204.

The duration of a sonication determines how much heat will actually be transferred to the target mass tissue at the focal spot. For a given signal power and focal spot diameter, a longer duration results in more heat transfer and, therefore, a higher temperature. Thermal conduction and blood flow, however, make the actual temperature distribution within the tissue unpredictable for longer sonication duration. As a result, typical implementations use duration of only a few seconds. In focused ultrasound systems, care must also be taken not to raise the temperature at the focal point too high. A temperature of 100° C. will cause water in the tissue to boil forming gas in the path of beam 112. The gas blocks the propagation of beam 112, which significantly impacts the performance of system 100.

Controller 106 controls the mechanical and electrical properties of transducer 102. For example, controller 106 controls electrical properties such as the frequency, duration, and amplitude of the electronic drive signal and mechanical properties such as the position of transducer 102. By controlling the position of transducer 102, the position of the focal spot within target mass 116 can be controlled. In one embodiment, controller 106 controls the x-position, z-position, the pitch, and the roll of transducer 102. A preferred mechanical positioning system for controlling the physical position of the transducer is taught in commonly assigned U.S. patent application Ser. No. 09/628,964, entitled "Mechanical Positioner for MRI Guided Ultrasound Therapy System," which is hereby incorporated by reference for all it teaches and discloses.

In one implementation, electromechanical drives under the control of controller 106 are used to control these positional aspects. It will be apparent to those skilled in the art that other implementations may employ other means to position transducer 102 including hydraulics, gears, motors, servos, etc. Additionally, it must be remembered that controlling the electrical properties, mainly frequency f and phase of transducer 102 controls the position of the focal spot along the y-axis of transducer 102 and the dimensions of the focal volume. Controller 106 uses properties provided by planner 108 to control the mechanical and electrical properties of transducer 102.

Planner 108 automatically constructs a treatment plan, which consists of a series of treatment site represented by thermal dose properties. The purpose of the treatment plan is to ensure complete ablation of target mass 104 by planning a series of sonications that will apply a series of thermal doses at various points within target mass 104, resulting in a composite thermal dose sufficient to ablate the entire mass.

For example, the plan will include the frequency, duration, and power of the sonication and the position and mode of the focal spot for each treatment site in series of treatment sites. The mode of the focal spot refers to the fact that the focal spot can be of varying dimensions. Typically, there will be a range of focal modes from small to large with several intermediate modes in between. The actual size of the focal spot will vary, however, as a function of the focal distance (l), the frequency and focal spot dispersion mode. Therefore, planner 108 must take the mode and focal spot size variation into account when planning the position of the focal spot for a treatment site. The treatment plan is then passed to controller 106 in the relevant format to allow controller 106 to perform its tasks.

In order to construct the treatment plan, planner 108 uses input from User Interface (UI) 110 and imager 114. For example, in one implementation, a user specifies the clinical application protocol, i.e., breast, pelvis, eye, prostate, etc., via UI 110. Selection of the clinical application protocol may control at least some of the default thermal dose prediction properties such as thermal dose threshold, thermal dose prediction algorithm, maximum allowed energy for each thermal dose, thermal dose duration for each treatment site, cooling time between thermal doses, and electrical properties for the heat applying element.

In other implementations, some or all of these properties are input through UI 110 as user specified thermal dose prediction properties. Other properties that may be input as user specified thermal dose prediction properties are the sonication grid density (how much the sonications should overlap) and the physical parameters of transducer 102. The latter two properties may also be defined as default parameters in certain implementations.

Additionally, a user may edit any of the default parameters via UI 110. In one implementation, UI 110 comprises a Graphical User Interface (GUI): A user employs a mouse or touch screen to navigate through menus or choices as displayed on a display device in order to make the appropriate selections and supply the required information.

To further aid planner 108 in constructing the treatment plan, imager 114 supplies images of target mass 104 that can be used to determine volume, position, and distance from skin surface 202. In a typical implementation, imager 114 is a Magnetic Resonance Imaging (MRI) device and, in one implementation, the images provided are three-dimensional images of target mass 104. Once planner 108 receives the input from UI 110 and the images from imager 114, planner 108 automatically constructs the treatment plan.

Figure 4:
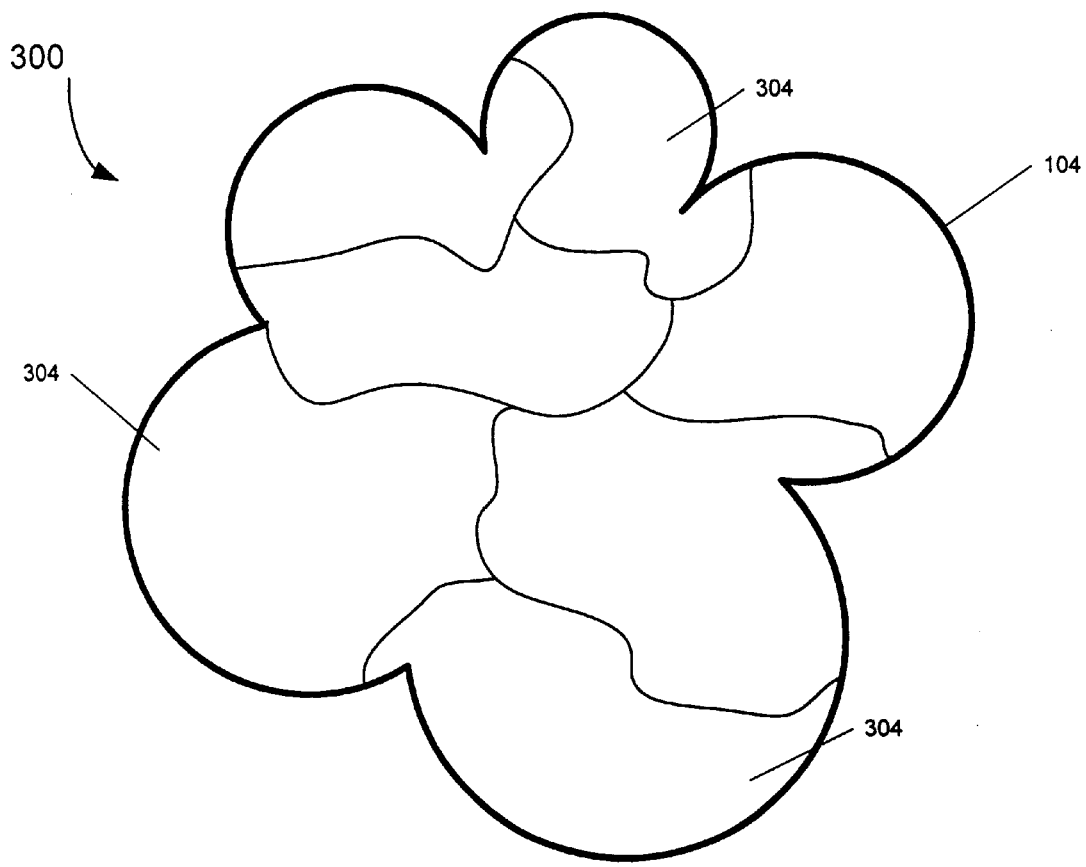
FIG. 4 is a cross-sectional view of a target tissue mass, illustrating a series of planned sonication areas.

As illustrated in FIG. 4, the goal of the treatment plan is to completely cover a target tissue mass 300 with a series of sonications 304 so that the entire target mass is fully ablated. In one implementation, once the treatment plan is constructed a user may, if required, edit the plan by using UI 110. In one implementation, planner 108 will also produce a predicted thermal dose distribution. This distribution is similar to the distribution illustrated in FIG. 4, wherein the predicted thermal doses 304 are mapped onto images of target mass 104 provided by imager 114. In one implementation, the distribution is a three-dimensional distribution. Additionally an algorithm is included in planner 108 that limits the peak temperature of the focal zone so as to prevent evaporation. The algorithm is referred to as the dose predictor.

Figure 5:
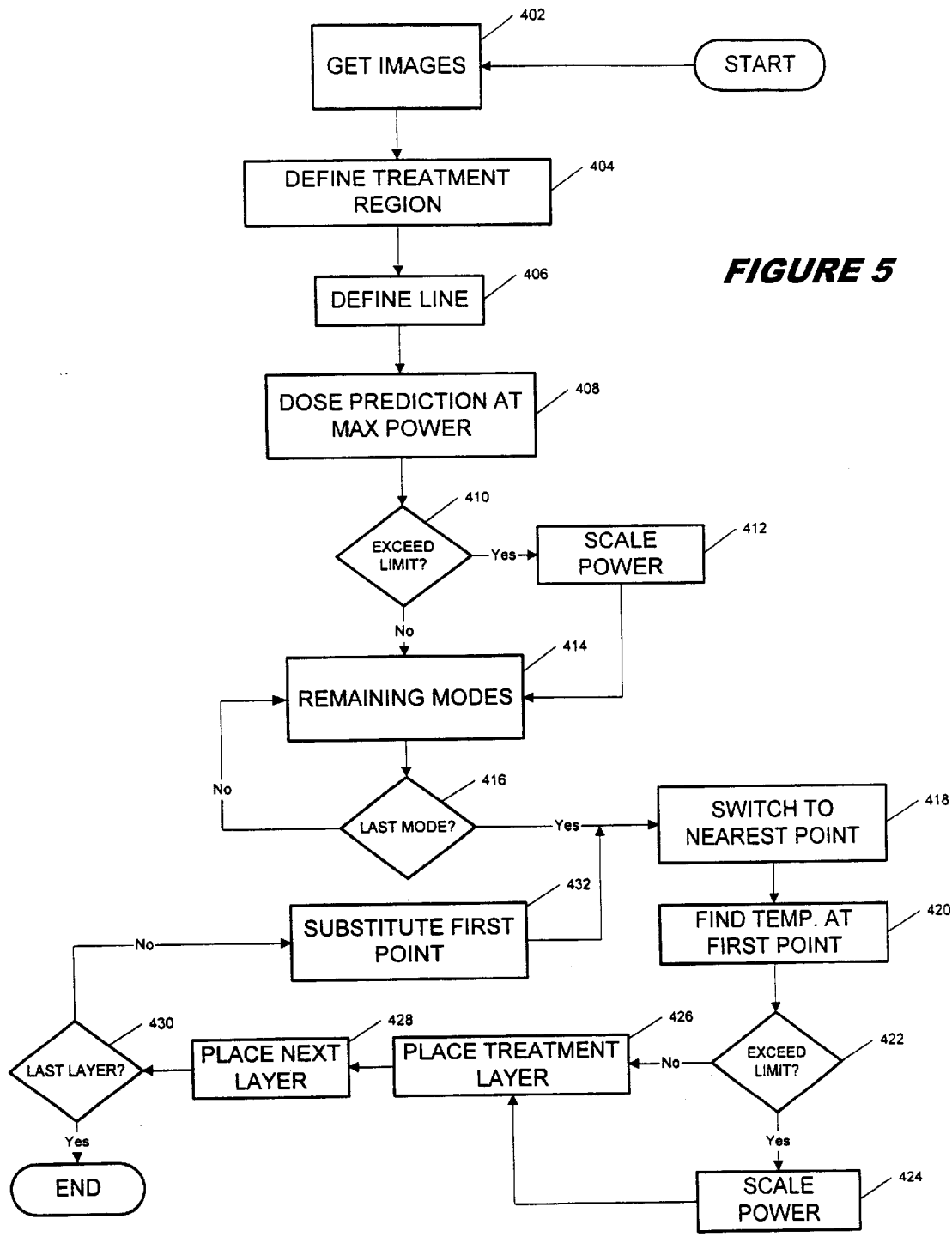
FIG. 5 is a preferred process flow diagram for constructing a three-dimensional treatment plan using the system of FIG. 2.

In one implementation, the treatment plan is a three-dimensional treatment plan. FIG. 5 illustrates one preferred process flow diagram for constructing a three-dimensional treatment plan, using three-dimensional images of target mass 104 and a three-dimensional predicted thermal dose distribution 300. The ability of focusing at different focal lengths (l) leads to variable focal spots and variable lesion sizes in target mass 104 as a function of (y), the transducer axis. Therefore, as a result of the process illustrated in FIG. 5, planner 108 finds a minimum number of overlapping cross-sectional treatment layers required to ablate a portion of target mass 104 extending from $y_{near}$ to $y_{far}$.

Planner 108 will also predict the lesion size in the cross-sectional layer and will provide the maximal allowed energy in each layer, taking into account the maximum allowed temperature rise. The energy or power will be normalized among different layers, such that the maximal temperature at the focus remains approximately constant throughout the treatment zone 206.

Constructing the three-dimensional treatment plan begins in step 402 with obtaining diagnostic quality images of the target mass. For example, the diagnostic quality images may be the preliminary images supplied by an imager such as imager 114. In step 404, planner 108 uses the diagnostic images to define the treatment region. Then, in step 406, a line $y=[y_{near}:y_{far}]$ is defined such that (y) cuts through target zone 206 perpendicular to transducer along the transducer axis from the nearest point within target mass 104 ($y_{near}$) to the furthest point ($y_{far}$). Line (y) will be the axis along which the treatment layers will be defined.

Once (y) is defined planner 108 will perform a dose prediction in step 408 using the maximal power required for small and large spot sizes at ($y_{far}$). In step 410, planner 108 determines if the resulting maximal temperature exceeds the allowed limit. It should be noted that properties such as the maximal power and the maximal temperature limit may be supplied as default thermal dose prediction properties or may be supplied as user supplied thermal dose prediction properties. If the resulting maximal temperature does exceed the allowable limit, the power is scaled down linearly in step 412 until the temperature elevation is within the allowable limit.

The small and large focal modes may correspond to modes 0 and 4, respectively, with additional modes 1, 2 and 3 falling between modes 0 and 4. Therefore, in step 414, planner 108 predicts the maximal power for the intermediate modes 1, 2 and 3, from the scaled max powers at modes 0 and 4. Thus, in step 416, if there are further modes, planner 108 reverts to step 408 and predicts the maximal power for these modes. If it is the last mode for ($y_{far}$) then planner 108 uses the same scaled max power, as in step 418, to find the corresponding maximal powers for each focal mode at ($y_{near}$). Then in step 420, planner 108 finds the maximal temperature elevation and lesion size for the appropriate mode and the required maximal power at a point ($y_l$), such that $y_{near}<y_l<y_{far}$. Preferably, ($y_l$) is close to ($y_{near}$). For example, in one implementation, $y_l=y_{near}+25$ mm. If the temperature elevation at ($y_l$) exceeds the allowable limit as determined in step 422, then in step 424 the power is scaled down until the temperature elevation is within the limit, and then planner 108 determines the resulting lesion size at ($y_l$).

Using an overlap criterion with respect to the ($y_{near}$) boundary, which may be provided via a sonication grid density, the first treatment is placed. The treatment will actually be a three-dimensional layer or slice. Then, in step 428, using an inter-layer overlap criterion, an auxiliary treatment slice is placed on top of the previous treatment layer using the same height for the second slice as for the first slice. In step 430, planner 108 determines if more layers are needed to reach ($y_{far}$). If more layers are needed, then the process reverts to step 418, and ($y_l$) replaces ($y_{near}$) (step 432) in the algorithm.

Once the last treatment layer is reached, planner 108 will determine if the layer extends beyond the target limit ($y_{far}$). If the layer does extend too far, then the overlap criterion should be used with the outer limit ($y_{far}$) as a boundary instead of the previous layer. Using ($y_{far}$) in the overlap criterion may cause overdose but will not damage healthy tissue outside target mass 104.

In one implementation, the thermal dose properties are automatically optimized using physiological parameters as the optimization criterion in one implementation mechanical tissue parameters like compressibility, stiffens and scatter are used.

Figure 6:
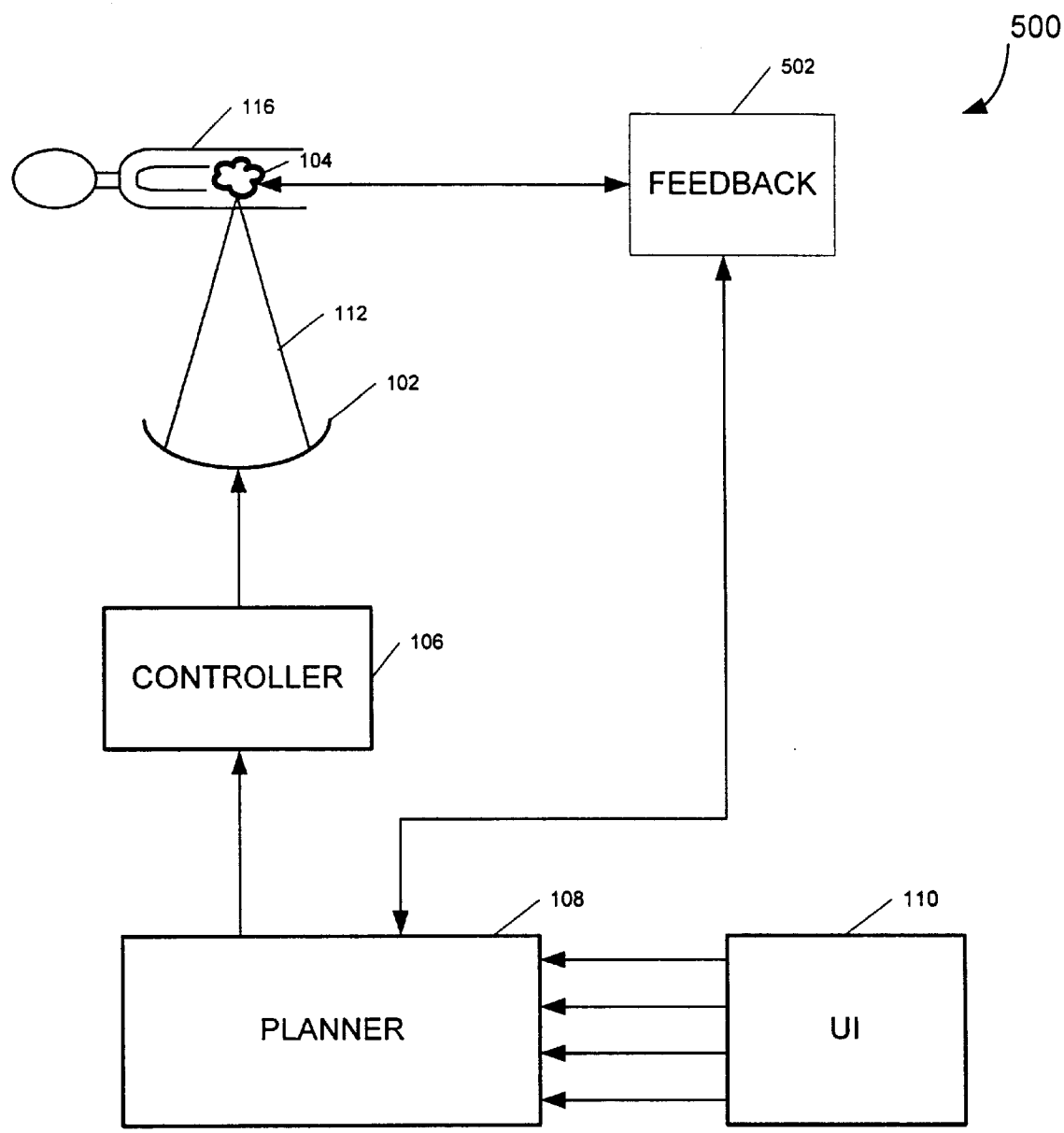
FIG. 6 is a simplified schematic block diagram of an alternate thermal treatment system comprising a feedback image generator.

Referring to FIG. 6, a thermal treatment system 500, similar to system 100 of FIG. 2, includes an online feedback imager 502. In practice, the actual thermal dose delivered with a particular sonication is not the same as the thermal dose predicted by planner 108. As mentioned previously, absorption coefficient blood flow, uneven heat conduction, different rates of conduction for different tissue masses, tissue induced beam aberration and variances in system tolerances make it difficult to accurately predict thermal dosages. Moreover, the actual focal spot dimensions are variable as a function of focal distance (l) and of focal spot dispersion, making accurate thermal dosing predictions even more difficult.

Figure 7A:
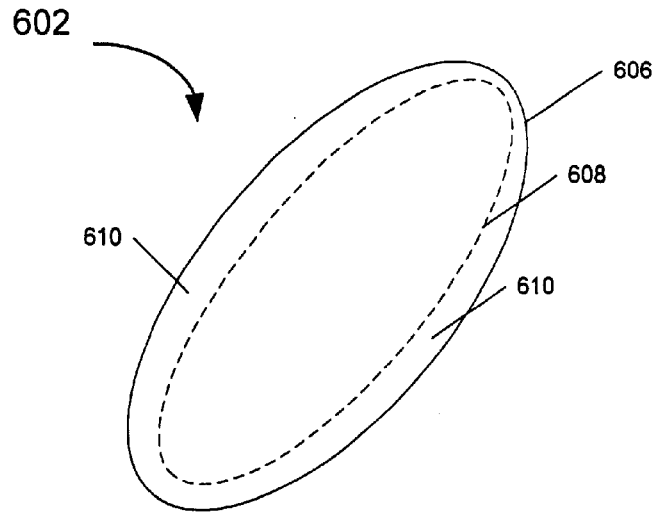
FIGS. 7A and 7B are two-dimensional representations of a target sonication areas, illustrating instances in which the actual thermal ablation is either greater than (FIG. 7A), or less than (FIG. 7B), the predicted amount.
Figure 7B:
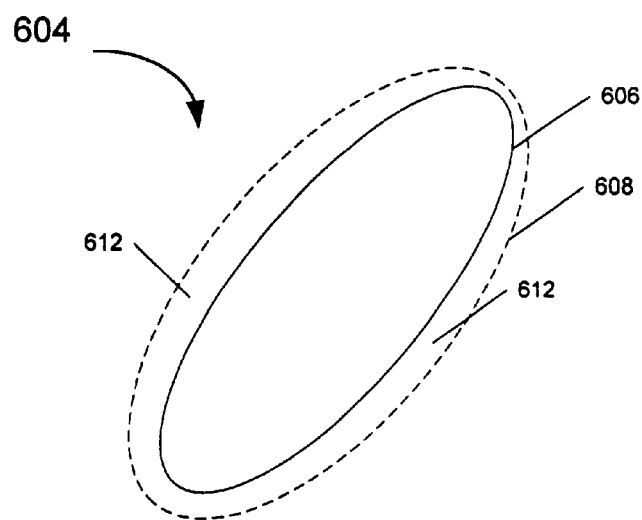

As illustrated in FIGS. 7A–B, the actual thermal dose 606 will often not ablate the predicted amount of tissue. In particular, two situations can occur. First, as illustrated by comparison 602 in FIG. 7A, actual thermal dose 606 may be larger than predicted thermal dose 608. In this case there will be an overlap of ablated tissue 610. The second situation is illustrated by comparison 604 in FIG. 7B. In this case, actual thermal dose 606 is smaller than predicted thermal dose 608. Therefore, there is an area 612 of non-ablated tissue remaining after sonication.

Figure 8:
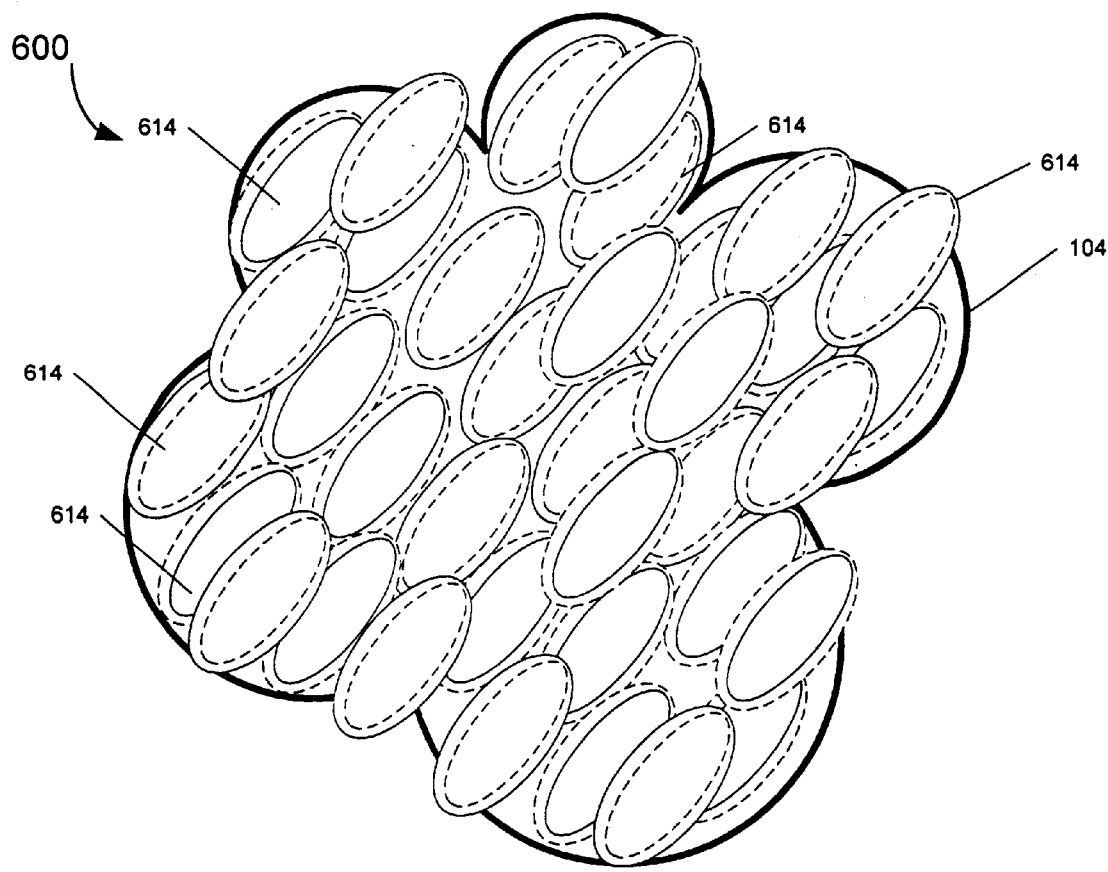
FIG. 8 illustrates a comparison of actual versus predicted thermal doses for an entire target tissue region constructed by the system of FIG. 6 using images from the feedback image generator.

The online feedback imager 502 provides real-time temperature sensitive magnetic resonance images of target mass 104 after some or all of the sonications. The planner 108 uses the images from the feedback imager 502 to construct an actual thermal dose distribution 600 comparing the actual composite thermal dose to the predicted composite thermal dose as illustrated in FIG. 8. In particular, thermal dose distribution 600 illustrates a comparison of the actual versus predicted thermal dose for each or some of the sonications. As can be seen, overlapping areas 610 and non-ablated areas 612 will result in over- or under-dosing as the treatment plan is implemented and thermal doses are applied to different treatment sites 614 within target mass 104.

In one implementation, the images provided by feedback imager 502 and the updated thermal dose distributions 600 represent three-dimensional data. Planner 108 uses thermal dose distribution 600 to automatically adjust the treatment plan, in real-time, after each sonication or uses the thermal dose distribution 600 in some of the points to adjust for the neighboring points. Planner 108 can adjust the treatment plan by adding treatment sites, removing treatment sites, or continuing to the next treatment site. Additionally, the thermal dose properties of some or all remaining treatment sites may automatically be adjusted by planner 108 based on real-time feedback from feedback imager 502.

As mentioned, planner 108 reformulates the treatment plan automatically after each thermal dose or after some of the sonication points, thus ensuring that target mass 104 is completely ablated in an efficient and effective manner. In addition, the feedback provided by online feedback imager 502 might be used to manually adjust the treatment plan or to override the changes made by planner 108. It should be noted that in one example embodiment, imager 114 also functions as feedback imager 502.

Figure 9:
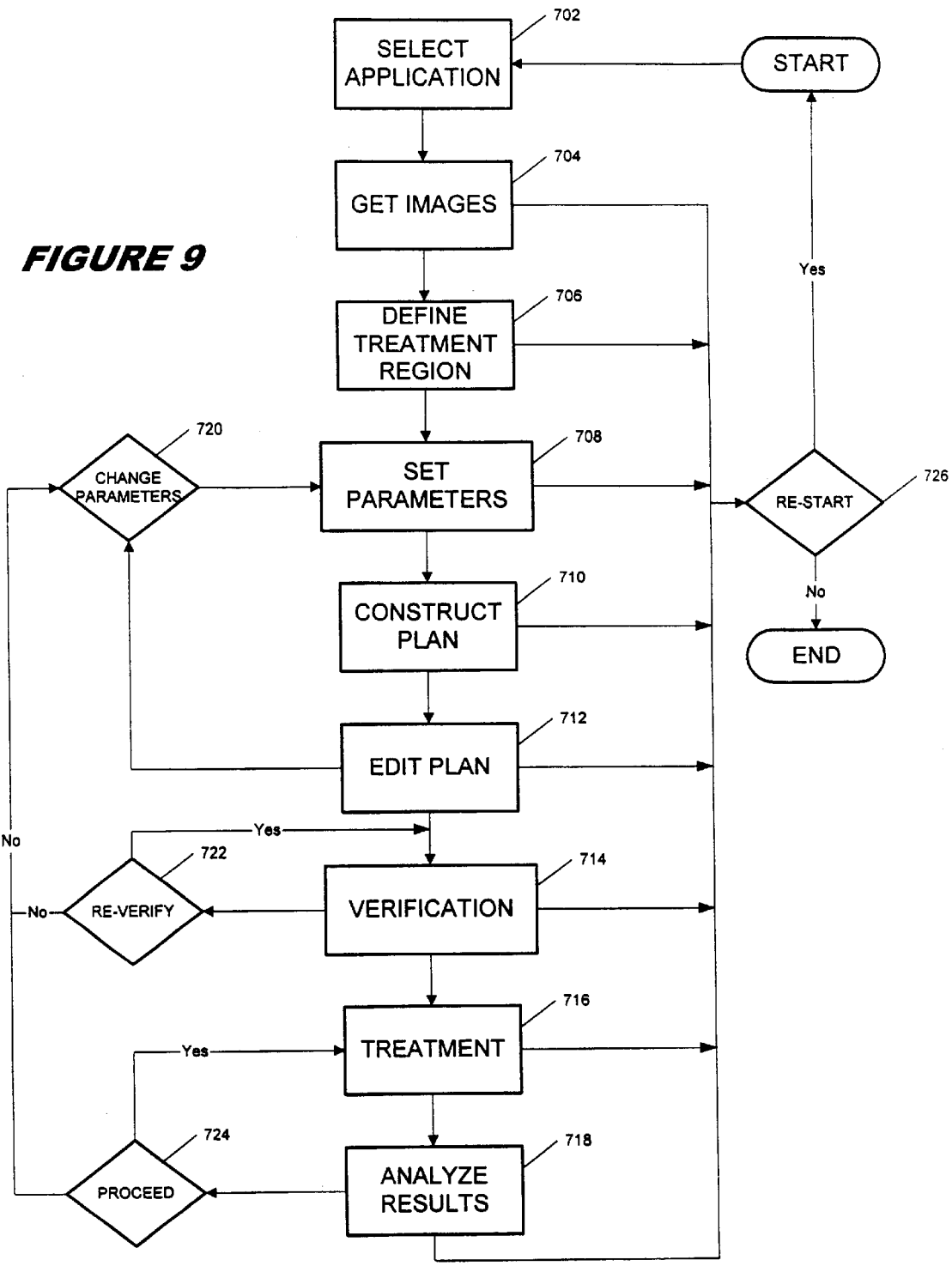
FIG. 9 illustrates a preferred method of controlling thermal dosing in a thermal treatment system.

A preferred method of controlling thermal dosing in a thermal treatment system (e.g., systems 100 and 500) is illustrated in FIG. 9. Initially, a user selects an appropriate clinical application protocol in step 702. For example, a user may use an interface such as UI 110 to select the clinical application protocol. In one embodiment, selecting the clinical application protocol controls a set of default thermal dose prediction parameters. After the clinical application is selected, relevant magnetic resonant images of a target mass are retrieved in step 704. For example, the images may be retrieved by a means such as imager 114. In step 706, the images are used to define a target region such as a treatment slice as discussed previously. In one embodiment, defining the target region involves manually or automatically tracing the target mass onto the images retrieved in step 704. In one implementation, the target mass is traced in three dimensions onto three-dimensional images for three-dimensional treatment planning. In another embodiment that uses ultrasound, the operator is allowed to account for obstacles such as bones, gas, or other sensitive tissue and plan accordingly to ensure that the ultrasound beam will not pass through these obstacles. Based on this planning, a patient may be repositioned or the transducer may be repositioned and/or tilted in order to avoid the obstacles.

In step 708, the user may enter additional thermal dose prediction properties or modify any default thermal dose prediction properties already selected. For example, these additional properties may be entered via UI 110. Then in step 710, a treatment plan is automatically constructed based on the properties obtained in the previous steps. The purpose of the treatment plan is to ensure a proper composite thermal dose sufficient to ablate the target mass by applying a series of thermal doses to a series of treatment sites, automatically accounting for variations in the focal spot sizes and in the thermal dose actually delivered to the treatment site.

The treatment plan may, for example, be automatically constructed by a planning means such as planner 108. In one embodiment, automatically constructing the treatment plan includes constructing an expected thermal dose distribution showing the predicted thermal dose at each treatment site. This thermal dose distribution may represent a three-dimensional distribution, and, in such an implementation, constructing the treatment plan may follow the steps illustrated in FIG. 5, and described above. In another embodiment, constructing the treatment plan further comprises calculating limits for the ultrasonic energy associated with each sonication so as to prevent evaporation.

In step 712, the treatment plan is edited by manual input. For example, UI 110 may be used to edit the treatment plan. In one embodiment, editing the plan may include adding treatment sites, deleting treatment sites, changing the location of some or all of the treatment sites, changing other thermal dose properties for some or all treatment sites, or reconstructing the entire plan. As illustrated by step 720, if the plan is edited, then the process reverts to step 708 and continues from there. Once the plan is set, then verification step 714 is performed. Verification is required to ensure that treatment system 100 is properly registered with regard to the position of the focal spot relative to patient 116 and target mass 104. In one embodiment, verification comprises performing a low energy thermal dose at a predefined spot within said target mass in order to verify proper registration. In a following step, the verification could be repeated at full energy level to calibrate the dosing parameters. As illustrated by step 722, re-verification may be required depending on the result of step 714. In this case, the process reverts back to step 714 and verification is performed again. On the other hand, mechanical properties, such as position, relating to transducer 102 may need to be changed (step 720) and, therefore, the process reverts to step 708.

Once the verification is complete, the treatment plan is implemented in step 716. In one embodiment, this step comprises capturing temperature sensitive image sequences of the target mass as each step of the plan is being implemented. These images will illustrate the actual thermal dose distribution resulting from each successive thermal dose. An online feedback imager 502 may, for example, provide the temperature sensitive images that are used to construct the actual thermal dose distribution. In step 718, the actual thermal dose distribution is compared with the predicted thermal dose distribution in order to determine how closely the actual treatments are tracking the treatment plan. Then in step 724, it is determined if the treatment can proceed to the next step (repeat step 716), or if changes must be made to the treatment plan. (step 720). The changes may be accomplished manually or automatically and may comprise adding treatment sites, deleting treatment sites, repeating treatment sites, or modifying specific thermal dose properties for some or all of the treatment sites.

There are several methods that are used to change or update the treatment plan. For example, at the end of each thermal dose, there may be regions within the target layer that are not covered by accumulated dose contours. These untreated areas are separated into individual regions. Each of these regions is then sent through the process, beginning with step 708, resulting in an updated treatment plan constructed to treat the remaining regions. The process will repeat until there are no more untreated regions.

Figure 10C:
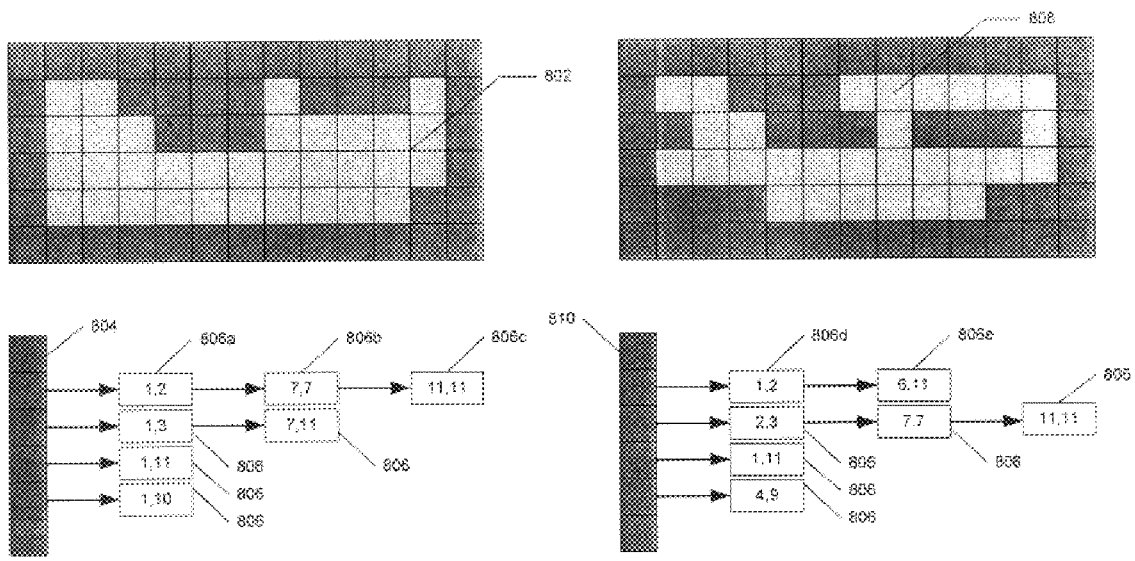
FIG. 10C illustrates a two dimensional pixel representation of a remaining untreated target tissue region derived by subtracting the pixel representation of FIG. 10B from the pixel representation of FIG. 10A.
Figure 10C:
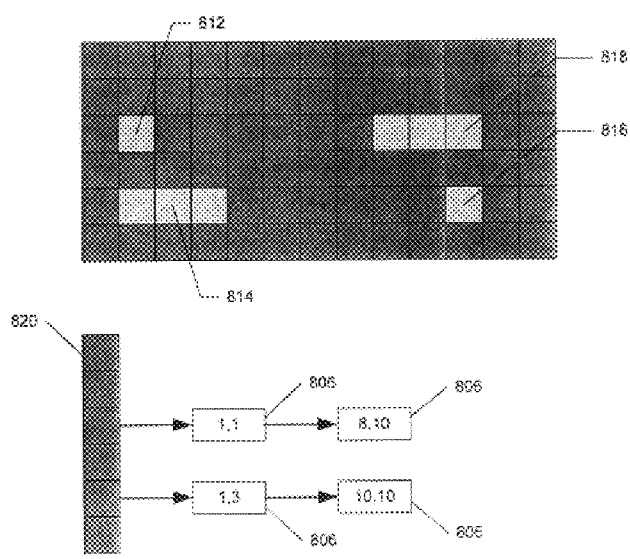

In order to accomplish the tracking of untreated regions, each treatment region may be maintained as a two-dimensional linked list of pixel ranges sorted by (y) and then (x) coordinates as illustrated in FIGS. 10A–C. As can be seen in FIG. 10A, the treatment region is a continuous region 802 represented by the lighter pixels. The pixel distribution is then represented by the data structure 804. This type of representation is called "run-length encoding." The data structure 804 contains linked lists 806 by row indicating the pixels that contain treatment region 802. Thus, for row 1, list element 806a indicates that the pixel range from 1 to 2 contains a portion of treatment region 802, 806b indicates that the pixel range from 7 to 7 contains a portion of treatment region 802, and 806c indicates that the pixel range from 11 to 11 contains a portion of treatment region 802. It can also be seen that rows 0 and 5 do not contain any portion of treatment region 802; therefore, these rows in data structure 804 do not contain any pixel ranges.

Once a thermal dose is applied, the area of the target mass that is destroyed (the treated region) is represented in the same fashion as the untreated region shown in FIG. 10A. The treated region (FIG. 10B) is subtracted from the untreated region in order to define the remaining untreated region within treatment region 802. These areas can then be sent back to the planning stage (step 720) and the treatment plan can be updated.

Subtraction of the run-lengths representing untreated region and the treated-region follows the following rules:

For run-length segments [a,b] and [c,d],

| [a,b]−[c,d] = | c > b or d < a | [a,b] | (1) |
|---|---|---|---|
| | c <= a and d >= b | 0 | (2) |
| | c > a and d >= b | [a, c − 1] | (3) |
| | c <=a and d < b | [d + 1, b] | (4) |
| | c > a and d < b | [a, c − 1] and [d + 1, b] | (5) |

The subtraction, therefore, of two regions involves traversing the lines in each region and subtracting a line in the first data structure from its corresponding line in the second data structure.

The above rules will be further explained by means of an example in which region 808 illustrated in FIG. 10B, and represented by data structure 810, will be subtracted from region 802 in FIG. 10A. Application of rules (1)–(5), for the given regions, results in the following:

| (Step 1) Top Row: | |
|---|---|
| [1,2] − [1,2] = 0 | Rule (2) |
| [7,7] − [1,2] = [7,7], [7,7] − [6,11] = 0 | Rules (1), (2) |
| [11,11] − [1,2] = [11,11], [11,11] − [6,11] = 0 | Rules (1), (2) |
| (Step 2) Second Row: | |
| [1,3] − [2,3] = [1,1], [1,1] − [7,7] = [1,1], [1,1] − [11,11] = [1,1] | Rules (3), (1), (1) |
| [7,11] − [2,3] = [7,11], [7,11] − [7,7] = [7,11], [7,11] − [11,11] = [7,10] | Rules (1), (1), (3) |
| (Step 3) Third Row: | |
| [1,11] − [1,11] = 0 | Rule (2) |
| (Step 4) Lower Row: | |
| [1,10] − [4,9] = [1,3] and [10,10] | Rule (5) |

In performing the subtraction, each segment 806*d* and 806*e* in row 1 of data structure 810 is subtracted from each segment 806*a*, 806*b*, and 806*c* in row 1 of data structure 804. Thus, as can be seen for the top row under Step 1 above, segment 806*d* is subtracted from segment 806*a* using Rule (2). The application of Rule (2) results in a run-length segment that contains no pixels, i.e., a range of 0. Intuitively, it can be seen that segment 806*d* is the same as segment 806*a* and that subtraction of the two should result in 0, as it does under Rule (2). Next, segment 806*d* is subtracted from segment 806*b*, using Rule (1). Intuitively, because the pixel range described by segment 806*d* does not overlap the range described by segment 806*b*, subtracting 806*d* from 806*b* should have no effect. Indeed, application of rule (1) has no effect on segment 806*b*.

Now, however, segment 806*e* must be subtracted from segment 806*b*. As can be seen, segment 806*e* overlaps segment 806*b* entirely. Therefore, application of rule (2), which is the appropriate rule for these two segments, results in 0. In other words, if region 802 is a target mass, and region 808 defines an expected thermal dose, then the dose represented by segment 806*e* will completely ablate the portion of the target mass represented by segment 806*b*. The same result occurs for the subtraction of segments 806*e* and 806*d* from segment 806*c*. The subtraction then continues for each row as illustrated by steps 2, 3, and 4 above. The resulting region is illustrated in FIG. 10C, which actually consists of four separate regions 812, 814, 816, and 818. These regions 812, 814, 816, and 818 are represented by data structure 820 and associated linked lists of run-length segments 806. It is these untreated regions 812, 814, 816, and 818 that will require the treatment plan to be updated by returning to the planning stage in step 720.

Figure 11:
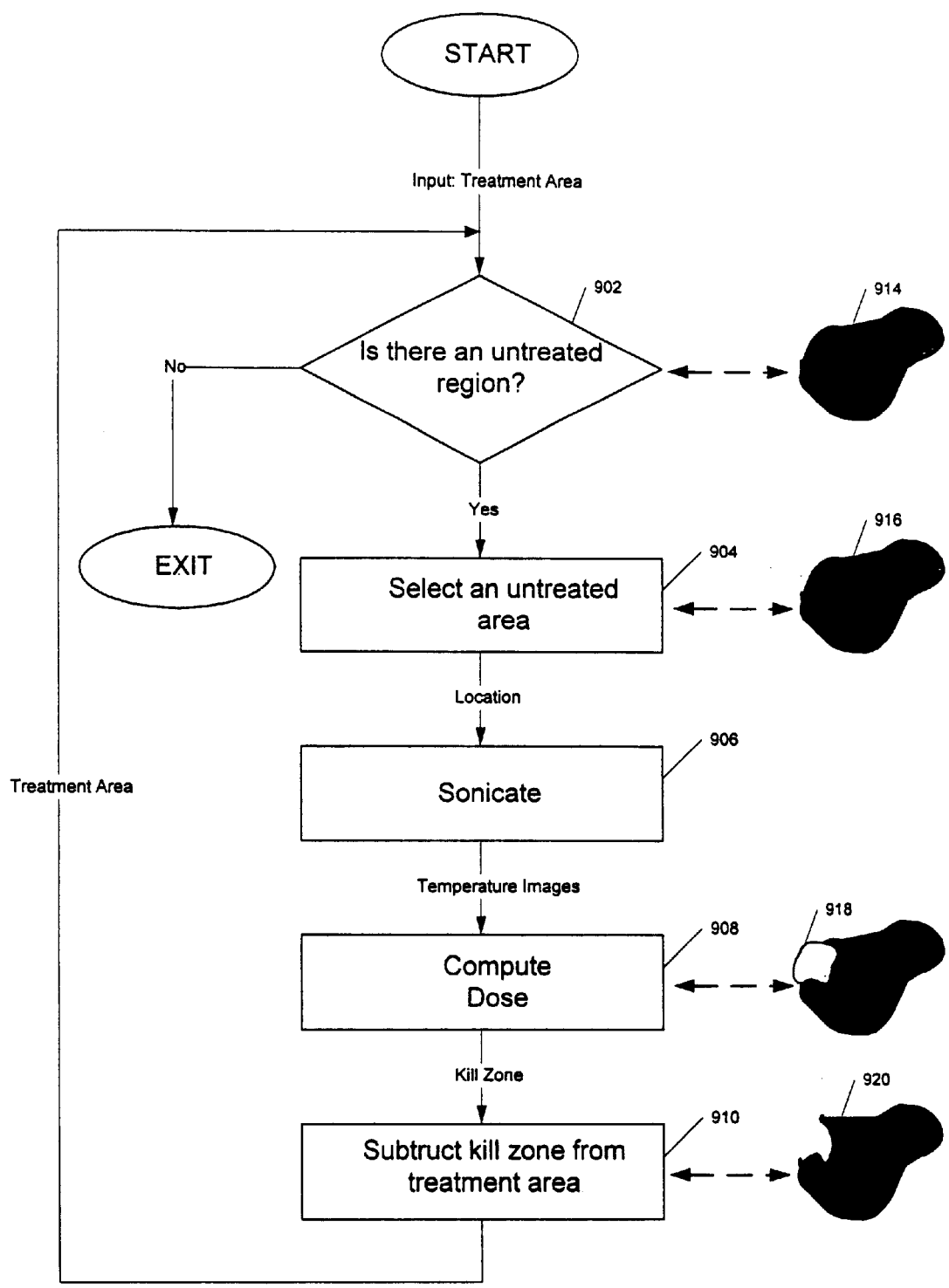
FIG. 11 illustrates a preferred method for updating a thermal treatment plan.

An alternative method for updating the treatment plan involves eliminating steps 710 and 712 in FIG. 9. Instead, the system accepts a target mass 914 to be treated and follows the steps illustrated in FIG. 11. First, in step 902, it is determined if there is an untreated region 914. If there is, then treatment site 916 is selected in step 904, and thermal dose properties are estimated so as to deliver the appropriate thermal dose the treatment site 916. Then, in step 906, the thermal dose is applied to treatment site 916 resulting in a treated region 918. In step 908, the size of treated region is calculated and stored as a linked-list so that in step 910 the treated region can be subtracted from the untreated region 920 in order to determine the remaining untreated region. The process then reverts to step 902, and a new treatment site is selected. Once the entire target mass 914 is treated, there will not be any untreated regions and the process will exit.

Referring back to FIG. 9, after the treatment is complete, it is determined in step 726 whether to restart a treatment or to exit. Additionally, if there is insufficient information or a fatal error occurs in any of steps 704–716, the process will automatically go to step 726, where it can be decide to proceed with a new treatment plan or to exit altogether.

Thus, on a most detailed and narrow aspect, the invention provides methods for constructing a three-dimensional thermal dose treatment plan, including:

(a) receiving diagnostic images;

(b) defining a target region;

(c) defining a treatment line that cuts through the target mass perpendicular to the surface of the heat applying element and extending from the nearest point within the target mass to the farthest;

(d) determining the maximal power required for a large and small focal spots at the furthest point;

(e) determining if the corresponding maximal temperatures for the large and small focal spots exceed the allowed limits;

(f) scaling the maximal power down until the maximal temperature is within the allowable limits, thus providing a scaled maximal power;

(g) using the scaled maximal power from the previous step to find maximal powers for any intermediate focal spot sizes;

(h) using the scaled maximal power to find the maximal powers for each focal spot size at the nearest point within the target mass along the treatment line;

(i) assuming the thermal dose is focused at a first point between the nearest point and farthest point, but preferably close to the nearest point;

(j) using the scaled maximal power to find maximal temperatures and a lesion size, corresponding to an appropriate focal spot size and required maximal power at the first point;

(k) determining if the maximal temperature at the first point is greater than the allowable limits;

(l) scaling down the maximal power at the first point so that the maximal temperature will not exceed the allowed limits;

(m) finding the corresponding lesion size at the first point;

(n) placing a first treatment slice using an overlap criterion with respect to a boundary defined by the nearest point in the target mass;

(o) placing an auxiliary treatment slice on top of the first treatment using an inter-layer overlap criterion; and (p) replacing the nearest point with the first point and returning to step (h) to repeat the process until the target region is covered from the nearest point to the farthest point along the treatment line.

Although many aspects and features of the present invention have been described and illustrated in the above description and drawings of the preferred embodiments, it is understood that numerous changes and modifications can be made by those skilled in the art without departing from the invention concepts disclosed herein.

The invention, therefore, is not to be restricted, except by the following claims and their equivalents.

What is claimed:

1. A thermal treatment system, comprising:

a heat applying element for generating a thermal dose used to ablate a target mass in a patient;

a controller for controlling thermal dose properties of the heat applying element;

an imager for providing preliminary images of the target mass;

a planner for automatically constructing a treatment plan, comprising a series of treatment sites that are each represented by a set of thermal dose properties;

wherein the planner automatically constructs the treatment plan based on input information including one or more of:

a volume of the target mass, a distance from a skin surface of the patient to the target mass, a set of default thermal dose prediction properties, a set of user specified thermal dose prediction properties, physical properties of the heat applying elements, and images provided by the imager.

2. The treatment system of claim 1, wherein the thermal dose properties translate, at least in part, to electrical and mechanical properties of the heat applying element.

3. The treatment system of claim 1, wherein the default thermal dose prediction properties are based on a type of clinical application and include at least one of:

thermal dose threshold, thermal dose prediction algorithm, maximum allowed energy for each thermal dose, thermal dose duration for each treatment site, cooling time between thermal doses, and electrical properties for the heat applying element.

4. The treatment system of claim 1, wherein the user specified thermal close prediction properties include at least one of overrides for any default thermal dose prediction properties, treatment site grid density, and thermal dose prediction properties not specified as default thermal dose prediction properties from the group comprised of thermal dose threshold, thermal dose prediction algorithm, maximum allowed energy for each thermal dose, thermal dose duration for each treatment site cooling time between thermal doses, and electrical properties for the heat applying element.

5. The treatment system of claim 1, wherein the treatment plan ensures that the entire target mass is covered by a series of thermal doses so as to obtain a composite thermal dose sufficient to ablate the entire target mass.

6. The treatment system of claim 1, wherein the thermal dose properties are automatically optimized using physiological properties as the optimization criterion.

7. The treatment system of claim 1, wherein the planner limits the thermal dose at each treatment site in order to prevent carbonization or evaporation.

8. The treatment system of claim 1, wherein the planner constructs a predicted thermal dose distribution illustrating the predicted thermal dose contours of each treatment site in the treatment plan.

9. The treatment system of claim 1, further comprising a User Interface (UI) for entering user specified thermal dose prediction properties and for editing the treatment plan once the treatment plan is constructed.

10. The treatment system of claim 1, wherein the treatment plan is constructed in three dimensions.

11. The treatment system of claim 1, further comprising a feedback imager for providing thermal images illustrating the actual thermal dose distribution resulting at each treatment site.

12. The treatment system of claim 11, wherein the imager acts as the feedback imager.

13. The treatment system of claim 1, wherein the heat applying element applies one of the following ultrasound energy, laser light energy, RF energy, microwave energy, and electrical energy.

14. A focused ultrasound system, comprising:

a transducer for generating ultrasound energy that results in thermal doses to ablate a target mass in a patient;

an imager for providing preliminary images of the target, and for providing thermal images illustrating an actual thermal dose distribution in the patient; and a planner for automatically constructing a treatment plan using the preliminary images, the treatment plan comprising a series of treatment sites represented by a set of thermal dose properties used by the controller to control the transducer;

wherein the planner further constructs a predicted thermal dose distribution illustrating the predicted thermal dose contours of each treatment site in the treatment plan;

wherein after a thermal dose is delivered to each treatment site in the treatment plan, the actual thermal dose distribution is compared to the predicted thermal dose distribution to determine remaining untreated locations within the target mass.

15. The focused ultrasound system of claim 14, wherein after a thermal dose is delivered to a treatment site in the treatment plan, the actual thermal dose distribution is compared to the predicted thermal dose distribution to determine changes to the dosing parameters in neighboring sonication sites.

16. The focused ultrasound system of claim 14, wherein the planner automatically evaluates the treatment plan based on the remaining untreated locations and updates the treatment plan to ensure complete ablation of the target mass is achieved by one or more of adding treatment sites, removing treatment sites, modifying existing treatment sites, or leaving the treatment plan unchanged.

17. The focused ultrasound system of claim 14, wherein a user can manually adjust the treatment plan based on the remaining untreated locations.

18. The focused ultrasound system of claim 14, wherein the preliminary images and the thermal images represent three-dimensional data.

19. The focused ultrasound system of claim 14, wherein the predicted thermal dose distribution and actual thermal dose distribution represent three-dimensional data.

20. The focused ultrasonic system of claim 14, wherein the imager further provides outlines of sensitive regions within the patient where ultrasonic waves are not allowed to pass.

21. The focused ultrasonic system of claim 20, wherein the processor uses the outlines in constructing the treatment plan so as to avoid exposing the sensitive regions to ultrasound.

22. The focused ultrasound system of claim 20, wherein the sensitive regions comprise bones, gas, and other sensitive tissues.

* * * * *